United States Patent
Roe

(10) Patent No.: US 8,480,633 B2
(45) Date of Patent: Jul. 9, 2013

(54) DRUG DELIVERY PUMP DRIVE USING A SHAPED MEMORY ALLOY WIRE

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/460,087

(22) Filed: Apr. 30, 2012

(65) Prior Publication Data

US 2012/0230845 A1    Sep. 13, 2012

Related U.S. Application Data

(62) Division of application No. 12/120,672, filed on May 15, 2008, now Pat. No. 8,172,811.

(51) Int. Cl.
*A61M 5/00* (2006.01)

(52) U.S. Cl.
USPC ........... 604/207; 604/152; 604/208; 604/211; 74/25

(58) Field of Classification Search
USPC ............................... 604/207, 208, 211; 74/25
See application file for complete search history.

(56) References Cited

U.S. PATENT DOCUMENTS

| | | |
|---|---|---|
| 381,160 A | 4/1888 | Moon |
| 1,258,368 A | 3/1918 | Smith |
| 2,722,613 A | 11/1955 | Culbertson et al. |
| 3,264,949 A | 8/1966 | Dietlin |
| 4,150,544 A | 4/1979 | Pachter |
| 4,282,442 A | 8/1981 | Massinger |
| 4,443,888 A | 4/1984 | Cutter |
| 4,586,335 A | 5/1986 | Hosoda et al. |
| 4,587,128 A | 5/1986 | Cummings |
| 4,660,431 A | 4/1987 | Heine |
| 4,711,157 A | 12/1987 | Kayyod et al. |
| 4,811,564 A | 3/1989 | Palmer |
| 4,829,843 A | 5/1989 | Suzuki |
| 4,945,779 A | 8/1990 | Williams |

(Continued)

FOREIGN PATENT DOCUMENTS

| | | |
|---|---|---|
| EP | 1130257 A2 | 9/2001 |
| WO | 03048571 A1 | 6/2003 |

(Continued)

OTHER PUBLICATIONS

PCT International Preliminary Report on Patentability dated Nov. 25, 2010 pertaining to International application No. PCT/EP2009/003234.

*Primary Examiner* — Emily Schmidt
(74) *Attorney, Agent, or Firm* — Dinsmore & Shohl, LLP

(57) ABSTRACT

A pump drive and a method thereof to dispense a liquid drug from a container having a plunger piston are disclosed. The pump drive provides a unidirectional clutch provided about a rotational axis which supports centrally a wheel. The clutch has an inner race operably connected to the plunger piston, wherein the clutch is configured to rotate both the inner race about the axis in unison with rotation of the wheel in only a first direction to advance the plunger piston, and to let the wheel rotate relative to the inner race about the axis in a second direction opposite to the first direction without advancing the piston plunger. The drive in one embodiment includes at least one shape memory alloy wire which when excited rotates the wheel in the first rotational direction to advance the piston plunger and dispense the liquid drug from the container.

4 Claims, 7 Drawing Sheets

U.S. PATENT DOCUMENTS

| | | | |
|---|---|---|---|
| 5,134,923 A | 8/1992 | Wexler | |
| 5,237,236 A | 8/1993 | Culp | |
| 5,543,678 A | 8/1996 | Hoiberg | |
| 5,575,790 A | 11/1996 | Chen et al. | |
| 5,622,482 A | 4/1997 | Lee | |
| 5,816,306 A | 10/1998 | Giacomel | |
| 5,919,167 A | 7/1999 | Mulhauser et al. | |
| 6,147,435 A | 11/2000 | Fujimura | |
| 6,179,569 B1 | 1/2001 | Kojima et al. | |
| 6,203,528 B1 | 3/2001 | Deckert et al. | |
| 6,244,228 B1 | 6/2001 | Kuhn et al. | |
| 6,249,717 B1 | 6/2001 | Nicholson et al. | |
| 6,375,638 B2 | 4/2002 | Nason et al. | |
| 6,404,098 B1 | 6/2002 | Kayama et al. | |
| 6,656,158 B2 | 12/2003 | Mahoney et al. | |
| 6,723,072 B2 | 4/2004 | Flaherty et al. | |
| 6,752,787 B1 | 6/2004 | Causey, III et al. | |
| 6,811,548 B2 | 11/2004 | Jeffrey | |
| 6,832,477 B2 | 12/2004 | Gummin et al. | |
| 6,851,260 B2 | 2/2005 | Mernoe | |
| 6,940,209 B2 | 9/2005 | Henderson | |
| 7,052,251 B2 | 5/2006 | Nason et al. | |
| 7,128,727 B2 | 10/2006 | Flaherty et al. | |
| 7,144,384 B2 | 12/2006 | Gorman et al. | |
| 2001/0034502 A1 | 10/2001 | Moberg et al. | |
| 2002/0005681 A1 | 1/2002 | Koopmann et al. | |
| 2003/0229310 A1 | 12/2003 | Flaherty et al. | |
| 2004/0176727 A1 | 9/2004 | Shekalim | |
| 2004/0220551 A1 | 11/2004 | Flaherty et al. | |
| 2005/0177111 A1 | 8/2005 | Ozeri et al. | |
| 2006/0037315 A1* | 2/2006 | Zanella et al. | 60/527 |
| 2007/0219480 A1 | 9/2007 | Kamen et al. | |

FOREIGN PATENT DOCUMENTS

| | | |
|---|---|---|
| WO | 2004056412 A2 | 7/2004 |
| WO | 2004082108 A1 | 9/2004 |
| WO | 2007020225 A1 | 2/2007 |

\* cited by examiner

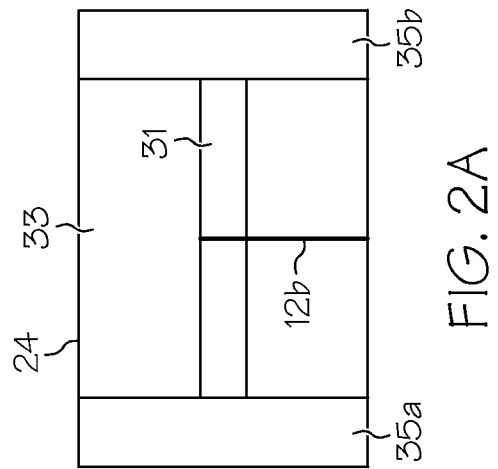
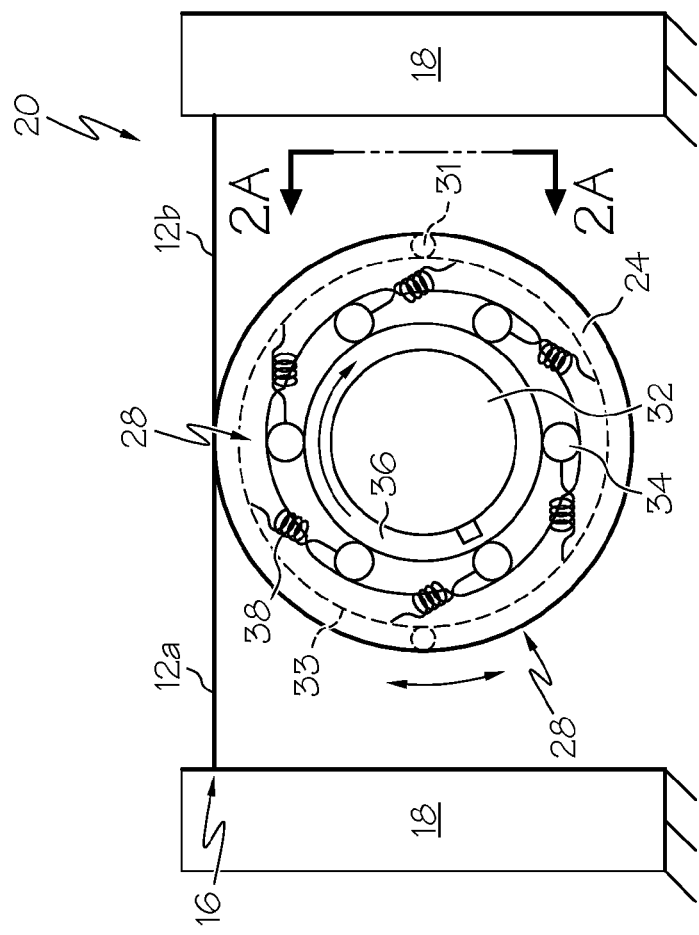

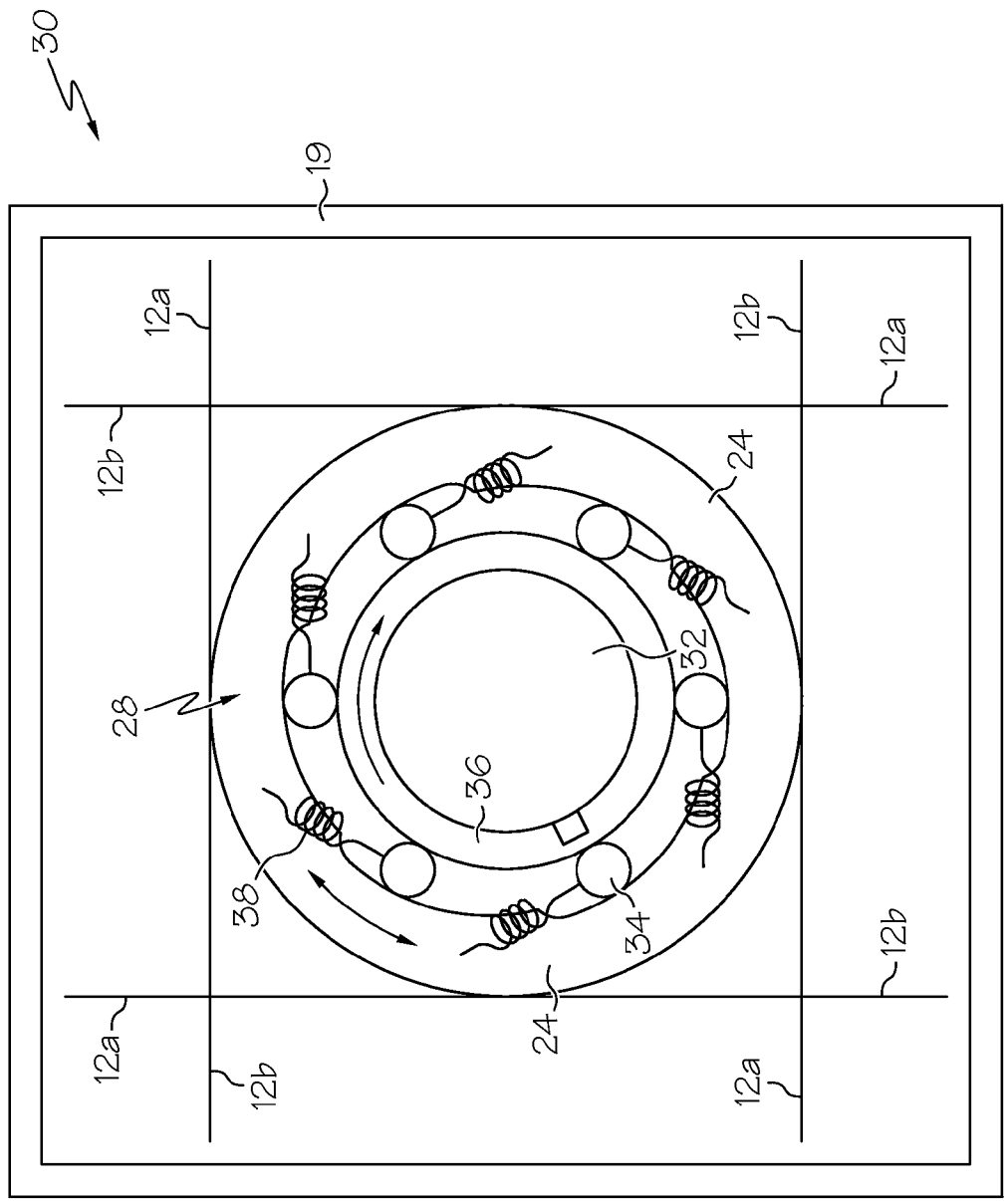

DRUG DELIVERY PUMP DRIVE USING A SHAPED MEMORY ALLOY WIRE

CROSS-REFERENCE TO RELATED APPLICATION

This application is a divisional of U.S. application Ser. No. 12/120,672 filed May 15, 2008 now U.S. Pat. No. 8,172,811.

FIELD OF THE INVENTION

The present invention is generally related drug delivery pumps, and in particular to a drug delivery pump drive using a shape memory alloy to advance a plunger piston to deliver a liquid drug from a container.

BACKGROUND OF THE INVENTION

Typically miniature drug delivery pumps use an electric motor and a system of many gears to reduce the high speed motors down to a slower speed. The slower speed provides the precision needed to control the very small doses of a liquid drug being delivered by means of an advancing lead screw and nut moving the syringe piston. Due to the above performance requirements, such miniature drug delivery pump use an expensive high quality electric motor and the associated high quality gears, therefore making such pumps expensive and generally not disposable in nature. In addition, concealment under clothing is problematic due the relative size of the motor and the noise generated during operation.

SUMMARY OF THE INVENTION

It is against the above background that the present invention provides a drug delivery pump drive which uses a shape memory alloy (SMA) to advance a plunger piston to deliver a liquid drug from a container and a method thereof. The small size of the SMA based pump drive helps to reduce overall size of the drug delivery pump, thereby resulting in a suitable wearable device. In addition, due to the low cost of the SMA based pump drive, the drug delivery pump may be disposable.

The present invention in one embodiment provides a SMA based pump drive for a miniature drug delivery pump having a single SMA wire used to drive a main wheel in a driven direction and a spring to rewind the main wheel after each drive cycle. In another embodiment, the SMA based pump drive provides a pair of SMA wires which are wrapped around the circumference of the main wheel in opposite directions and connected thereto so that one SMA wire rotates the main wheel clockwise and the other SMA wire rotates the wheel counter clockwise when excited sequentially. In another embodiment, the SMA based pump drive provides a plurality of the above mentioned opposed pairs of the SMA wires. In still another embodiment of the SMA based pump drive, a SMA wire is provided in a linear solenoid arrangement with a spring return to provide reciprocating linear motion. A set of concentric (inner and outer) tubes having matching facing helical slots with bearings therebetween is provided to convert the reciprocating linear motion into reciprocating rotary motion. As the SMA wire and spring return linearly reciprocate, pulling the inner tube therewith, the helical slots and bearings between the inner and outer tubes cause the outer tube to rotate a few degrees back and forth for each drive cycle. The outer tube being connected to the main wheel, transfers this clockwise and counterclockwise (reciprocating rotary) motion for each drive cycle to the main wheel. Inside the main wheel is a unidirectional clutch which converts the reciprocating rotary motion of the main wheel into rotational motion in a single direction. This rotational motion in a single direction is used to advance a lead screw and push the plunger piston to dispense the liquid drug from the container.

In another embodiment, a pump drive used to dispense a liquid drug from a container having a plunger piston is disclosed. The pump drive comprises a unidirectional clutch provided about a rotational axis and supporting centrally a wheel. The unidirectional clutch has an inner race operably connected to the plunger piston, wherein the unidirectional clutch is configured to rotate both the inner race about the rotational axis in unison with rotation of the wheel in only a first rotational direction which advances the plunger piston, and to let the wheel rotate relative to the inner race about the rotational axis in a second rotational direction opposite to the first rotational direction without advancing the plunger piston. The pump drive also includes at least one shape memory alloy wire providing a motor force when excited to rotate the wheel in at least the first rotational direction.

In still another embodiment, a pump drive used to dispense a liquid drug from a container having a plunger piston is disclosed. The pump drive comprises a lead screw having a rotational axis and being operably connected to the plunger piston wherein rotation of the lead screw about the rotational axis advances the piston plunger in a dispensing direction which dispenses the liquid drug from the container, a wheel, and a unidirectional clutch provided about the rotational axis and supporting centrally the wheel. The unidirectional clutch has an inner race connected centrally to the lead screw, wherein the unidirectional clutch is configured to rotate both the inner race and lead screw about the rotational axis in unison with rotation of the wheel in only a first rotational direction, and to let the wheel rotate relative to the inner race without rotating the lead screw about the rotational axis in a second rotational direction opposite to the first rotational direction. The pump drive further includes at least one shape memory alloy wire providing a motor force when excited to rotate the wheel in at least the first rotational direction.

In another embodiment, a pump drive use to dispense a liquid drug from a container having a plunger piston is disclosed. The pump drive comprises a unidirectional clutch provided about a rotational axis and supporting centrally a wheel. The unidirectional clutch has an inner race operably connected to the plunger piston, wherein the unidirectional clutch is configured to rotate both the inner race about the rotational axis in unison with rotation of the wheel in only a first rotational direction which advances the plunger piston, and to let the wheel rotate relative to the inner race about the rotational axis in a second rotational direction opposite to the first rotational direction without advancing the plunger piston. The pump drive also includes a linear drive to rotate the wheel in the second rotational direction, and a pair of inner and outer concentric tubes with helical slots and bearings therebetween located about the axis of rotation. In this embodiment, the linear drive acts on the inner tube in opposition such that the inner tube reciprocates with linear motion along the axis of rotation, wherein the helical slots and bearings cause the outer tube to reciprocate with rotary motion about the axis of rotation as the inner tube reciprocates with linear motion along the axis of rotation, and wherein the outer tube is connected to the wheel such that the rotary motion of the outer tube causes the wheel to rotate in the first rotational direction and then in the second rotational direction.

In another embodiment, a method of dispensing a liquid drug from a container having a plunger piston is disclosed. The method comprises providing a unidirectional clutch about a rotational axis which supports centrally a wheel, the unidirectional clutch having an inner race operably connected to the plunger piston, wherein the unidirectional clutch both rotates the inner race about the rotational axis in unison with rotation of the wheel in only a first rotational direction which advances the plunger piston, and lets the wheel rotate relative to the inner race about the rotational axis in a second rotational direction opposite to the first rotational direction without advancing the plunger piston. The method also includes providing a motor force by exciting at least one shape memory alloy wire which rotates the wheel in at least the first rotational direction.

In still another embodiment, a method of dispensing a liquid drug from a container having a plunger piston is disclosed. The method comprises providing a unidirectional clutch about a rotational axis which supports centrally a wheel, the unidirectional clutch having an inner race operably connected to the plunger piston, wherein the unidirectional clutch both rotates the inner race about the rotational axis in unison with rotation of the wheel in only a first rotational direction which advances the plunger piston, and lets the wheel rotate relative to the inner race about the rotational axis in a second rotational direction opposite to the first rotational direction without advancing the plunger piston; providing a linear drive to rotate the wheel in the second rotational direction. The method also includes providing a pair of inner and outer concentric tubes with helical slots and bearings therebetween located about the axis of rotation, wherein the linear drive acts on the inner tube in opposition such that the inner tube reciprocates with linear motion along the axis of rotation, wherein the helical slots and bearings cause the outer tube to reciprocate with rotary motion about the axis of rotation as the inner tube reciprocates with linear motion along the axis of rotation, and wherein the outer tube is connected to the wheel such that the rotary motion of the outer tube causes the wheel to rotate in the first rotational direction and then in the second rotational direction.

In yet another embodiment, a method of dispensing a liquid drug from a container having a plunger piston is disclosed. The method comprises providing a lead screw having a rotational axis and operably connecting the lead screw to the plunger piston wherein rotation of the lead screw about the rotational axis advances the piston plunger in a dispensing direction which dispenses the liquid drug from the container, providing a wheel, and providing a unidirectional clutch to support the wheel about the rotational axis. The method further includes connecting an inner race of the unidirectional clutch centrally to the lead screw, wherein the unidirectional clutch is configured to rotate both the inner race and lead screw about the rotational axis in unison with rotation of the wheel only in a first rotational direction, and to let the wheel rotation relative to the inner race without rotating the lead screw about the rotational axis in a second rotational direction opposite to the first rotational direction; providing at least one shape memory alloy wire which when excited provides a motor force to rotate the wheel in at least the first rotational direction; and exciting the shape memory alloy wire.

These and other features and advantages of the invention will be more fully understood from the following description of various embodiments of the invention taken together with the accompanying drawings.

BRIEF DESCRIPTION OF THE DRAWINGS

The following detailed description of the various embodiments of the present invention can be best understood when read in conjunction with the following drawings, where like structure is indicated with like reference numerals and in which:

FIG. 2 is an end view of another embodiment of a SMA based pump drive according to the present invention having an opposed pair of SMA wires and a unidirectional clutch;

FIG. 2A is a section view of the embodiment shown by FIG. 2 and taken along section line 2A-2A;

FIG. 3 is an end view of still another embodiment of a SMA based pump drive according to the present invention having a plurality of opposed pairs of SMA wires and a unidirectional clutch;

DETAILED DESCRIPTION

It is against the above background that the present invention provides a miniature drug delivery pump which uses a shape memory alloy (SMA) based pump drive to advance a syringe plunger to deliver a liquid drug from a container. The present invention has a cost and size advantage compared to traditional miniature drug delivery pumps and is a very compact and potentially disposable pump device design due to cost.

In the following description of the embodiments of the invention, skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention. Accordingly, the drawings are merely schematic representations, intending to depict only typical embodiments of the invention, and therefore should not be considered as limiting the scope of the invention. The invention will be described with additional specificity and detail through the accompanying drawings. The description of the invention may contain, for example, such descriptive terms as up, down, top, bottom, forward, back, clockwise, counterclockwise, right, or left. These terms are meant to provide a general orientation of the parts of the invention and are not meant to be limiting as to the scope of the invention.

Referring now to FIGS. 1-4, various illustrative embodiments of the SMA based pump drive according to the present invention are shown, and generally indicated by symbols 10, 20, 30, and 40, respectively. All of these embodiments of the SMA based pump drive 10, 20, 30, and 40 are reciprocating in design which converts linear motion of at least one SMA wire into unidirectional rotary motion.

Shape memory alloys are metals which exhibit two very unique properties, pseudo-elasticity, and a shape memory effect due to the metals having Martensite (unheated, deformable state) and Austenite (heated, original shape recovering state) phase changes. In most shape memory alloys, a temperature change of only about 10° C. is necessary to initiate the phase change (Martensite to Austenite) to recover an original size and shape of the wire after elongation and deformation. Alloys used as a shape memory alloy (SMA) wire include, for example and not limited thereto, copper based alloys, such as for example, copper-zinc-aluminum-nickel, copper-aluminum-nickel, iron-manganese-silicon alloys, and nickel-titanium (NiTi) alloys. The present invention in all embodiments uses at least one SMA wire as a prime mover for a unidirectional clutch which turns in one direction a lead screw which translates a plunger piston to dispense a liquid, such as a drug, from a container or cartridge.

Figure 1:
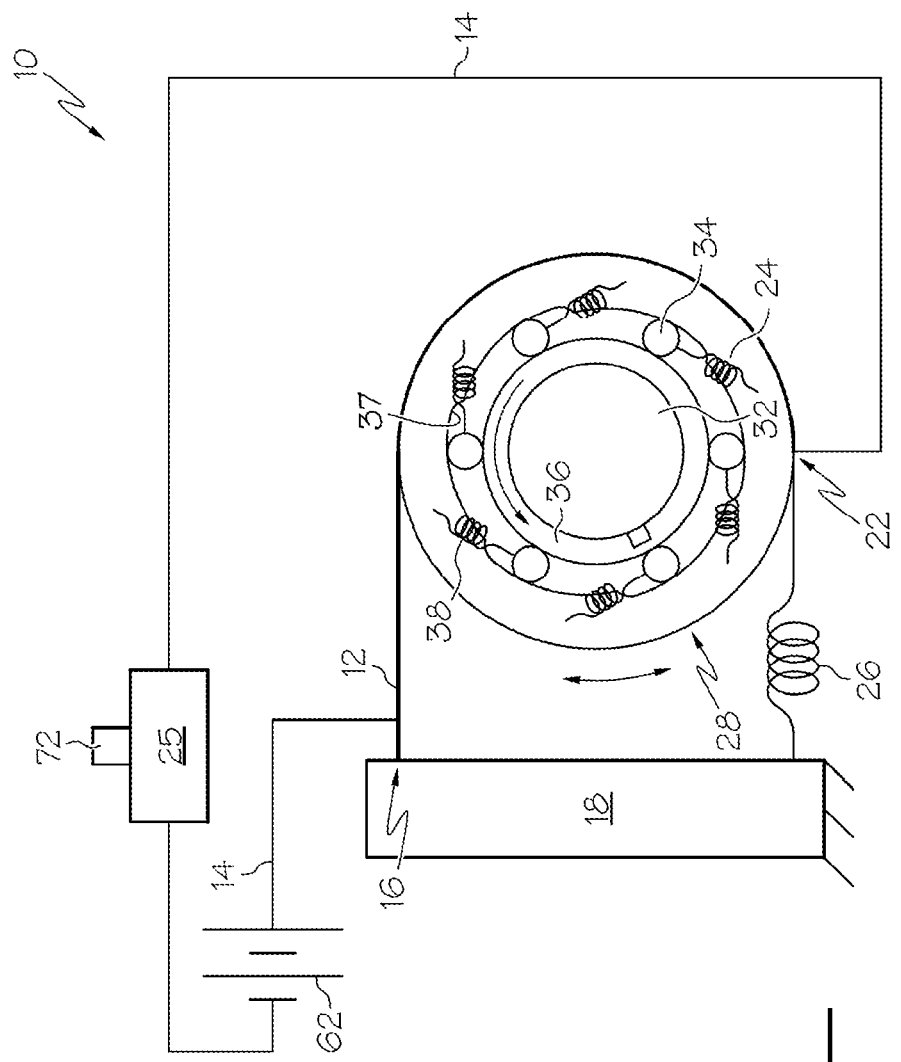
FIG. 1 is an end view of one embodiment of a SMA based pump drive according to the present invention having a single SMA wire with a spring return and a unidirectional clutch.
Figure 1A:
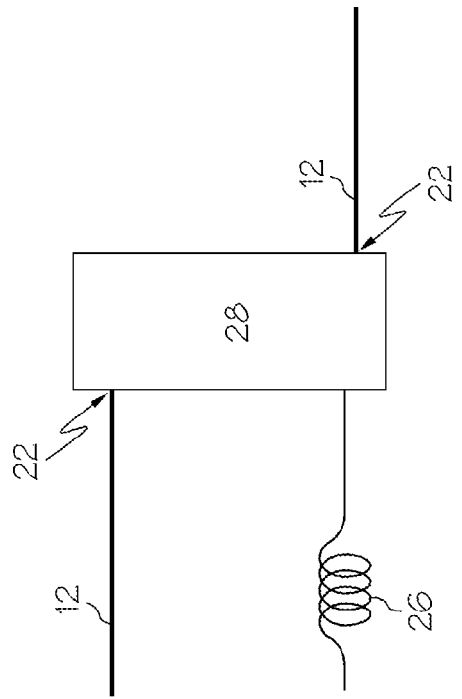
FIG. 1A is a schematic view of one embodiment of a SMA based pump drive according to the present invention having a plurality of SMA wires with a spring return and a unidirectional clutch.

In the first illustrated embodiment of the SMA based pump drive 10 shown by FIG. 1, a shape memory alloy (SMA) wire 12 is fixed at one end 16 to a support 18. The other end 22 of the SMA wire 12 is wrapped around the circumference of and connected to a main wheel 24 (i.e., an outer race) of a unidirectional clutch 28. Excitation (heating) of the SMA wire 12 causes the SMA wire 12 to work to regain its original size and shape, i.e., shorten in length, which rotates the main wheel 24 in a first direction about an axis of rotation, indicated by symbol "X". After excitation and cooling below the Martensite phase temperature, a spring 26 re-deforms by bending and elongating the SMA wire 12, and rotates the main wheel 24 in a second opposed direction about the axis of rotation X to complete a drive cycle. As shown, the spring 26 is also attached to the support 18 at one end and to the main wheel 24 at the other end at a point which places the spring 26 in opposition to the contraction of the SMA wire 12 when in the Austenite phase.

In the SMA based pump drive 10 shown by FIG. 1, as with the other embodiments of the SMA based pump drive 20, 30, and 40 (FIGS. 2, 3, and 4, respectively), the excitation of the SMA wire 12 is effected by the application of electrical energy from a battery 62 via conductors 14 which creates heat through the resistance of the SMA wire 12 itself. The application of the electrical energy from the battery 62 is controlled by a controller 25 which is configured to switch the electrical energy on and off. In one embodiment, the switching is a timed pulse when commanded by a user to operate, such as for example, via a push button 72. In one embodiment, pushing the push button 72 results in the controller 25 switching the electrical energy from the battery 62 on and off such that the SMA wire 12 will complete the correct number of drive cycles to release a defined quantity of the liquid drug. For example, in one embodiment, a push of the push button 72 causes the release of a dose of 0.5 ml of insulin. In other embodiments, other dosages per push of the push button 72 are also possible, which may range from 0.1 ml to 1 ml, and will depend on the programming/circuitry of controller 25, degrees of rotation of the main wheel 24 effected by the SMA wire 12, the transmitted torque of the unidirectional clutch 28 to a lead screw 32, and threading 41 between the lead screw 32 and a nut portion 43 of a plunger piston 44 (FIG. 6), which advances a plunger piston 44 to dispense the liquid drug from a drug container 46 (FIG. 5)

It is to be appreciated that in the SMA based pump drives 10, 20, and 30 (FIGS. 1-3, respectively), each SMA wire 12 is orientated adjacent the axis of rotation X of the main wheel 24, and in one particular embodiment, substantially perpendicular to the axis of rotation X. In addition, in the embodiments shown by FIGS. 1-3, each SMA wire 12 is wrapped around at least half of the circumference of the main wheel 24 with the end 22 of the SMA wire 12 coupled directly thereto. For example, in the illustrated embodiments shown in FIGS. 2 and 3, each SMA wire 12 extends about three quarters of the way around the circumference of the main wheel 24 and is coupled to a spoke 31 as best shown by FIG. 2A, which is a side portion view of the main wheel 24 taken along section line 2A-2A in FIG. 2. In one embodiment, the spoke 31 is situated above a surface portion 33 of the main wheel 24 that is recessed below the outermost circumference of the main wheel 24 and extends in a direction parallel to the axis of rotation X. In one embodiment the outermost circumference of the main wheel 24 is defined by front and rear face plate portions 35a and 35b, respectively. As shown in FIG. 2A, the spoke 31 spans between and is mounted at respective ends to the front and rear face plate portions 35a and 35b. The SMA wire 12 connects to the spoke 31 in a conventional fashion, such as for example, and not limited thereto, welding, screwing, wrapping, clamping, etc.

As shown by FIG. 2, for this embodiment of the SMA based pump drive 20, an opposed pair of SMA wires 12a and 12b are connected at their first ends to a respective support 18. At their other ends, the SMA wires 12a and 12b are connected to the main wheel 24 in opposition, such that the excitation of one wire will deform the other and vice-versa, thereby causing cycling of the main wheel 24 in a clockwise and counter clockwise fashion. As the SMA wires 12a and 12b are electrically energized and controlled as described above with reference to the conductors 14, the controller 25, and the battery 62 shown by FIG. 1, for brevity and ease of illustration, no further discussion or showing thereof in FIG. 2 is provided.

With reference now to FIG. 3, for this SMA based pump drive 30, a plurality of opposed pairs of SMA wires 12a and 12b are connected around a frame 19 and the circumference of the main wheel 24. In this illustrated embodiment, each of the SMA wires 12a and 12b is also wrapped at least half way around the main wheel 24 and connected thereto, such as via spokes 31 as shown in the embodiment depicted in FIG. 2A. The other end of each SMA wire 12a and 12b is connected to and about the frame 19 such that opposed pairs of the SMA wires 12a and 12b act in opposition to each other in the same manner as shown in FIG. 2, e.g., providing clockwise rotation and then providing counterclockwise rotation, or vice versa. In an alternative embodiment, a counteracting spring 26, such as shown by FIG. 1, is provided either singularly or a plurality replacing one side of the SMA wires 12a or 12b about the frame 19 and main wheel 24, such that the SMA wires provide rotation in a first direction (e.g., clockwise) and the spring(s) 26 provides rotation in a second direction (e.g., counterclockwise). It is to be appreciated that in comparison to the SMA based pump drives 10 and 20 (FIGS. 1 and 2, respectively), if similar sized SMA wires are used, the SMA based pump drive 30 of FIG. 3 would provide a larger torque due to the greater number of similarly sized SMA wires 12. Accordingly, thinner, lower cost SMA wire 12 may be used in the SMA based pump drive 30 than the single or double SMA wire embodiments shown by FIGS. 1 and 2, and still produce a desired torque. In addition, the SMA based pump drive 30 provides a more robust system than the single and double SMA wire embodiments shown by FIGS. 1 and 2, due to the fact that should any of the SMA wires 12a or 12b encounter mechanical failure, the other remaining opposed pairs of SMA wires 12a and 12b will continue to provide sufficient torque to rotate the main wheel 24 under the provided load and generate the motor force needed to push a plunger piston of a liquid drug container. Accordingly, the SMA based pump drive 30 may be useful in health situations in which redundancy and reliability of delivering a liquid drug is needed. As the opposed pairs of plurality of SMA wires 12a and 12b are electrically energized and controlled as described above with reference to FIG. 2, and via a plurality of the respective conductors 14 tied in parallel to the controller 25 and the battery 62 shown by FIG. 1, for brevity and ease of illustration, no further discussion or showing thereof in FIG. 3 is provided.

Figure 4:
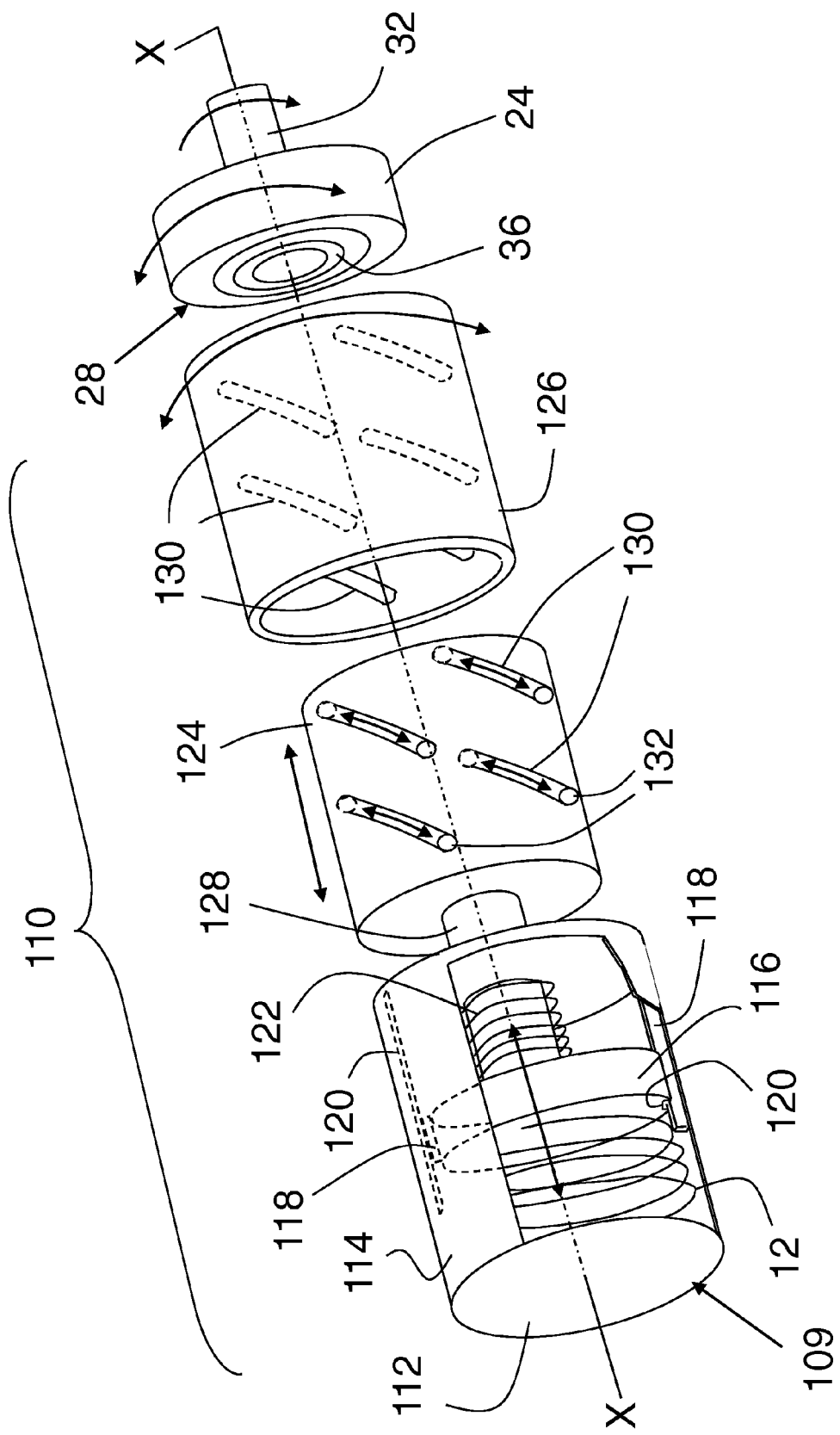
FIG. 4 is an exploded view of yet another embodiment of a SMA based pump drive according to the present invention having a coiled SMA wire with a spring return driving a pair of concentric tubes and a unidirectional clutch.
Figure 5:
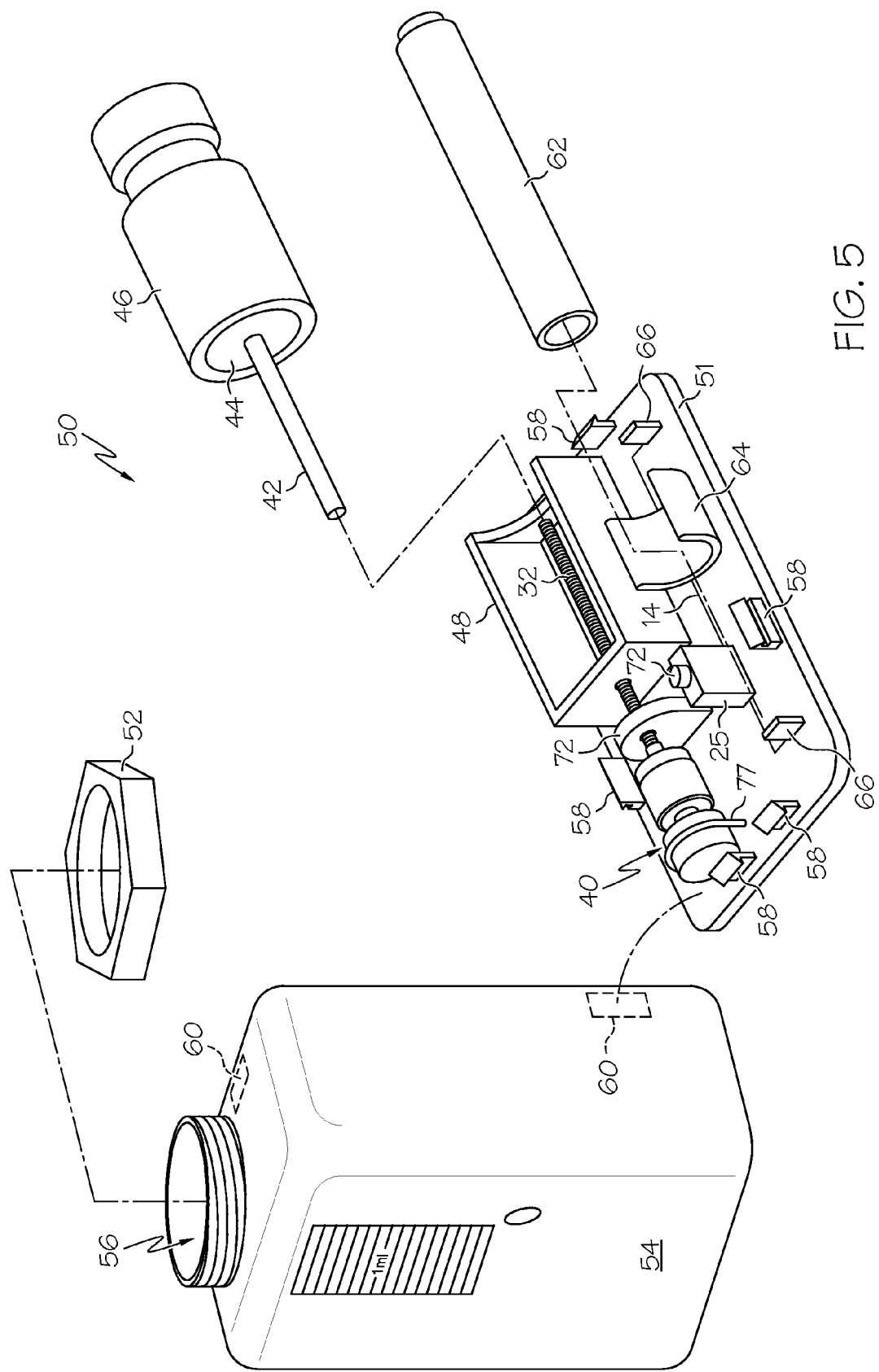
FIG. 5 is an exploded view of an embodiment of a miniature drug delivery pump according to the present invention and shown with the SMA based pump drive shown by FIG. 4.

For the SMA based pump drive 40 illustrated by FIG. 4, the SMA wire 12 is provided as a coil in a linear drive 109 and orientated along the axis of rotation X of the main wheel 24. The SMA wire 12 is operably coupled to the main wheel 24 via a linear solenoid arrangement, indicated generally by symbol 110, which includes the linear drive 109. In an alternative embodiment, the linear drive 109 shown in the FIG. 4 may be replaced with an electro-magnetic solenoid with a spring return, if faster fluid delivery is a desire.

In the illustrated embodiment, the linear drive 109 includes an actuator body 112, which is shown with a portion of a side wall 114 removed to show the interior components thereof. Housed within the actuator body 112 is the coiled SMA wire 12 and a plunge rod 116. The plunge rod 116 is housed slidably within the actuator body 112 and fixed for linear (back and forth) motion by a rail portion 118 provided on the side wall 114 engaged with a slot 120 provided on the plunge rod 116. Alternatively, the rail portion 118 may be provided on the plunge rod 116 and the slot 120 provided on the side wall 114, wherein this alternative arrangement is illustrated by the shown hidden lines within the actuator body 112.

The linear drive 109 of the solenoid arrangement 110 also include a spring return 122 to provide the reciprocating linear motion after excitation of the coiled SMA wire 12 as explained above in a previous section. In the illustrated embodiment, the spring return 122 is a spring housed also within the actuator body 112 in opposition to (i.e., biased against) the Austenite phase of the coiled SMA wire 12. A set of concentric inner and outer tubes 124 and 126, respectively, is also provided by the linear solenoid arrangement 110. An extension portion 128 of the plunge rod 116, which extends outwardly and centrally from the actuator body 112 connects centrally along the axis of rotation X to the inner tube 124. In this manner, the reciprocating linear motion of the plunge rod 116, due to movement from excitation of the coiled SMA wire 12 and the opposite motion thereafter from the spring return 122, is transferred to the inner tube 124.

The set of concentric inner and outer tubes 124 and 126 are provided with matching facing helical slots 130 having bearings 132 therebetween, which convert the reciprocating linear motion of the inner tube 124 into reciprocating rotary motion of the outer tube 126. As the plunge rod 116 linearly reciprocates, pulling the inner tube 124 therewith, the bearings 132 between the inner and outer tubes roll in their respective helical slots 130 causing the outer tube 126 to rotate a few degrees back and forth for each drive (push-pull) cycle of the plunge rod 116. The outer tube 126 being connected to the main wheel 24, transfers this clockwise and counterclockwise (rotational) motion for each drive cycle to the main wheel 24.

In one embodiment, the unidirectional clutch 28 is a one-way roller clutch or Sprag clutch; however, the invention is not limited in this respect and may find application with other unidirectional clutches. In such an embodiment, as the back and forth oscillation of the main wheel 24 occurs, the unidirectional clutch 28 alternately slips in one direction and then grabs in the opposite direction for each drive cycle of the SMA wire 12. As the unidirectional clutch 28 turns in the non-slip direction, the lead screw 32, which is connected centrally along the axis of rotation X to the clutch 28, also turns in the non-slip direction.

For example and with reference to FIG. 1, as the main wheel 24 rotates in the clockwise direction, clutch rollers 34 jam between the main wheel 24 and the inner race 36, locking them together. This locking action allows the angular displacement of the main wheel 24 to be transmitted to the lead screw 32. As the main wheel 24 rotates in an opposite (counterclockwise) direction, springs 38 between the clutch rollers 34 and inner race 36 are compressed, relieving the jam (i.e., releasing the locking action) to permit the clutch rollers 34 to slip. As the clutch rollers 34 slip, the main wheel 24 rotates freely about the inner race 36 such that no counterclockwise angular displacement of the main wheel 24 is transmitted to the lead screw 32.

Thus, in this embodiment, the clutch 28 transmits angular displacement of the main wheel 24 to the lead screw 32 only if the main wheel 24 and inner race 36 move in the clockwise direction when the clutch rollers 34 are wedged (jammed) between the surface of their respective tilted slope pockets 37 of the main wheel 24 and outer surface of the inner race 36.

With reference to FIG. 5, an exploded view of an embodiment of a miniature drug delivery pump, generally indicated by symbol 50 is shown, for example, with the SMA based pump drive 40 shown by FIG. 4. In all embodiments, the unidirectional rotational motion of the lead screw 32 also causes rotation about the nut portion 43 of the plunger 42 causing linear movement (translation) of the plunger 42 along the axis of rotation X in a dispensing direction. Translation of the plunger 42 in the dispensing direction advances the plunger piston 44 to dispense a liquid drug from the drug container 46.

As shown, the drug container 46 is accommodated in a cradle 48 of a base 51 of the drug delivery pump 50. In one embodiment, the drug container 46 is removable from the cradle 48 of the drug delivery pump 50, via removing a removable cap 52 from a cover 54 of the drug delivery pump 50 which permits removing and replacing the drug container 46 via an opening 56 defined in the cover 54. In such an embodiment, the opening 56 and/or the drug container 46 may be keyed or provided in shape which ensures proper alignment of the plunger piston 44 with the plunger 42. In another embodiment, the drug container 46 is not removable as the drug delivery pump 50 in such an embodiment is intended to be disposable after fully dispensing the liquid drug from the drug container 46.

In the illustrated embodiment of FIG. 5, the cover 54 snaps onto the base 51 without requiring separate cover fasteners via projections 58 of a pliable material which extend from the base 51 and resiliently seat into notches 60 provided in the inside surface of the cover 54. In an alternative embodiment separate cover fasteners may be provided.

The battery 62 is also provided to power the SMA based pump drive 40 of the drug delivery pump 50. The battery 62 in the illustrated embodiment is a size AAAA, which is about 42.5 mm long and about 8.3 mm in diameter, weighing around 6.5 grams. Output of alkaline batteries in this size is 1.5 volts, 625 mA·h. Although elements in the figures may be exaggerated in portion to other components, it is to be appreciated that the approximate relative size between the drug delivery pump 50 and the battery 62 is intended to be shown in the embodiment illustrated by FIG. 5. Accordingly, as shown the drug delivery pump 50 is not much larger than the AAAA battery 62, and is in one embodiment about 61 mm long, about 32 mm wide, and 15.5 mm in height, and weighs about one ounce, with the drug container 46 holding 2 ml of a liquid drug. Such dimensions of the drug delivery pump 50 is about one fourth the size of existing conventional pumps. The small size and weight of the drug delivery pump 50 makes it easier for the patient to hold the delivery pump in place, such via an adhesive on the skin and/or to conceal the delivery pump under clothing.

The battery 62 is held in a battery cradle 64 provided in the base 51 and contacts electrical terminal posts 66. The conductors 14 of the SMA based pump drive 40 each connect between a respective one of the electrical terminal posts 66 and the controller 25. A hole 70 is provided in the cover 54 such that the push button 72 may be depressed to energize the SMA wire 12 of the SMA based pump drive 40. It is to be appreciated that other electrical/IC components are provided, but are not shown for convenience of illustration as the actual control and electrical system of the drug pump is not the focus of the present invention.

The lead screw 32 which extends through and supports the main wheel 24 and the unidirectional clutch 28 about the axis of rotation X, is supported in turn by a base support 76 and the cradle 48. In addition, one or more of the projections 58 may serve to support the SMA based pump drive 40 against rearward thrust, which may further be support in other directions (e.g., up, side-to-side) by other supports, such as a strapping 77. In this manner, motion by the SMA base pump drive 40, which is counter to the thrust and torque provided by the lead screw 32 when rotated along the axis of rotation X, is minimized.

Figure 6:
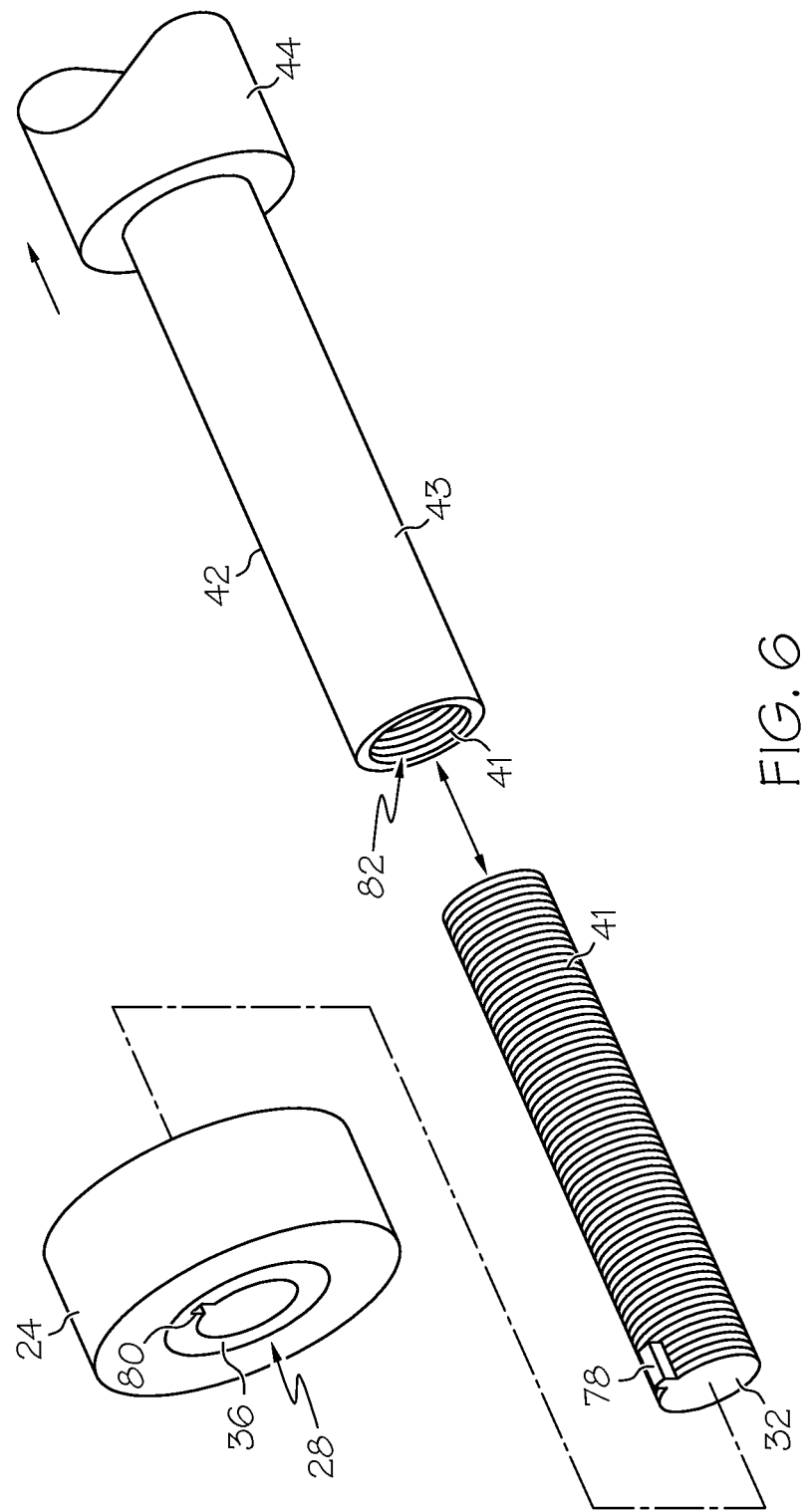
FIG. 6 is an exploded view of particular components of a SMA based pump drive and their arrangement thereof according to the present invention.

With reference to FIG. 6, an exploded view of particular components of a SMA based pump drive and their arrangement thereof according to an embodiment of the present invention is shown. The lead screw 32 in one embodiment has a key portion 78 which fits into a slot 80 provided in the inner race 36, such that the lead screw 32 rotates only with the inner race 36. The lead screw 32 is accommodated in a threaded cavity 82 of the nut portion 43 of the plunger 42. As the SMA wire 12 of the pump drive is energized by depressing the push button 72 (FIG. 7), the lead screw 32 rotates and advances out of the threaded cavity 82 along the rotational axis X causing movement of the plunger 42. As mentioned above previously, movement of the plunger 42 (i.e., translational along the rotational axis X) advances the plunger piston 44 into the drug container 46 (FIG. 5) to dispense a liquid drug therefrom. It is to be appreciated that in an alternative embodiment, the arrangement of the lead screw 32 and the plunger 42 used to push the plunger piston 44 is reversed. In such an alternative embodiment, the lead screw 32 provides the threaded cavity 82 in which a threaded outer diameter (not shown) of the plunger 42 is accommodated. In still another embodiment, the inner race 36 of the clutch 28 provides the threaded cavity 82 which acts directly on the threaded outer diameter of the plunger 42.

Figure 7:
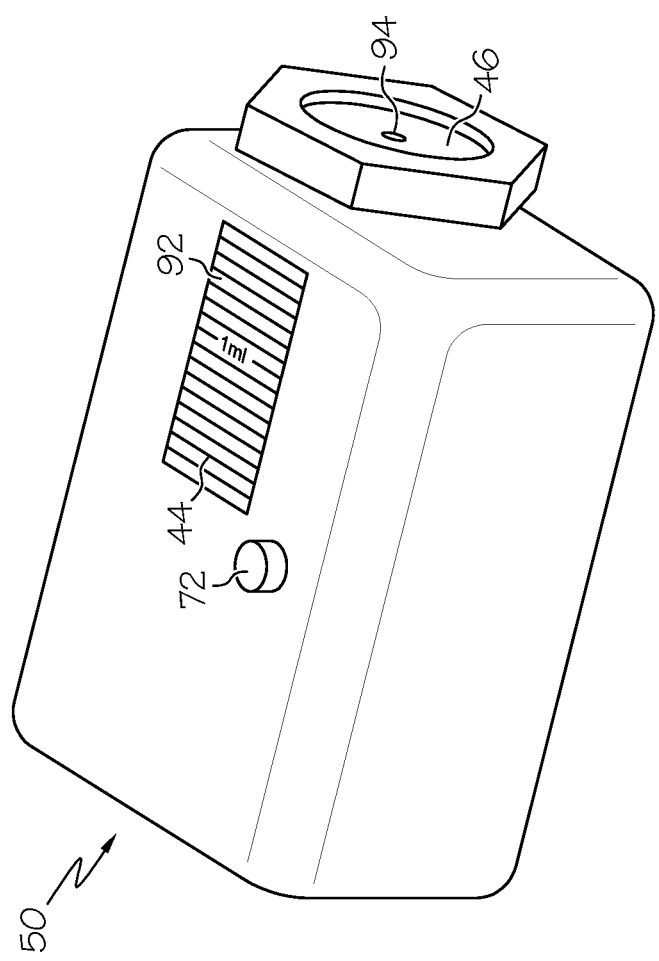
FIG. 7 is a perspective view of the miniature drug delivery pump embodiment shown by FIG. 5 according to the present invention with an administration set.

As shown by FIG. 7, in one embodiment, the drug delivery pump 50 provides a scaled window 92 through which a portion of the plunger piston 44 is visible and by which the patient in one embodiment uses to meter the delivery of a relatively large dose of the liquid drug. In another embodiment, dispensing of very small amounts of the liquid drug can be provided by controlling the pump drive with a timed switching circuit of the controller 25, wherein depressing push button 72 activates the timed switching circuit which energizes the pump drive for a predetermined period per button push. The drug container 46 includes an injection site 94 which is used to connect a spike connector 96 of an administration set 98 to the drug delivery pump 50. The spike connector 96 is connected to a fluid conduit 100 which at the distal end connects to a catheter 102, which enters the patient's intravenous system through the skin for delivery of the liquid drug.

Although not limited to, some of the noted advantages of the present invention are as follows: the inherent precision of the motion from the SMA wire which can be used to accurately deliver very small doses (i.e., about 0.01 ml), the ability to run at high frequency (up to 1 hz) to deliver quickly a large dose (i.e., about 1.0 ml), nearly silent operation, fewer moving parts, and inexpensive parts. Such advantages result in an overall compact and low cost drug delivery pump for the consumer.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A pump drive used to dispense a liquid drug from a container having a plunger piston, said pump drive comprising:
   a lead screw having a rotational axis and being operably connected to the plunger piston, wherein rotation of the lead screw about the rotational axis advances the piston plunger in a dispensing direction which dispenses the liquid drug from the container;
   a wheel;
   a unidirectional clutch provided about the rotational axis and supporting centrally the wheel, the unidirectional clutch having an inner race connected centrally to the lead screw, wherein the unidirectional clutch is configured to rotate both the inner race and lead screw about the rotational axis in unison with rotation of the wheel in only a first rotational direction, and to let the wheel rotate relative to the inner race without rotating the lead screw about the rotational axis in a second rotational direction opposite to the first rotational direction;
   a spring to rotate the wheel in the second rotational direction; and
   a plurality of shape memory alloy wires to provide the motor force when excited to rotate the wheel in at least the first rotational direction;
   wherein the spring is connected directly to the wheel and the plurality of shape memory alloy wires are also connected directly to the wheel.

2. The pump drive according to claim 1, wherein the plurality of shape memory alloy wires are each mounted laterally to the wheel and wherein the spring is mounted laterally to the wheel and acting in opposition to the plurality of shape memory alloy wires to provide the motor force to rotate the wheel in the second rotational direction.

3. The pump drive according to claim 1, wherein the shape memory alloy wire is wrapped around at least half the circumference of the wheel.

4. A method of dispensing a liquid drug from a container having a plunger piston, said method comprises:
   providing a lead screw having a rotational axis and operably connecting the lead screw to the plunger piston wherein rotation of the lead screw about the rotational axis advances the piston plunger in a dispensing direction which dispenses the liquid drug from the container;

providing a wheel;

providing a unidirectional clutch to support the wheel about the rotational axis;

connecting an inner race of the unidirectional clutch centrally to the lead screw, wherein the unidirectional clutch is configured to rotate both the inner race and lead screw about the rotational axis in unison with rotation of the wheel only in a first rotational direction, and to let the wheel rotation relative to the inner race without rotating the lead screw about the rotational axis in a second rotational direction opposite to the first rotational direction;

providing a plurality of shape memory alloy wires which when excited provides a motor force to rotate the wheel in at least the first rotational direction;

providing a spring to rotate the wheel in the second rotational direction; and exciting the plurality of shape memory alloy wires;

wherein the spring is connected directly to the wheel and the shape memory alloy wires are also connected directly to the wheel.

* * * * *

UNITED STATES PATENT AND TRADEMARK OFFICE
CERTIFICATE OF CORRECTION

| | | |
|---|---|---|
| PATENT NO. | : 8,480,633 B2 | Page 1 of 1 |
| APPLICATION NO. | : 13/460087 | |
| DATED | : July 9, 2013 | |
| INVENTOR(S) | : Steven N. Roe | |

It is certified that error appears in the above-identified patent and that said Letters Patent is hereby corrected as shown below:

In the Specification

Col. 1, Line 12, "generally related drug delivery" should read
--generally related to drug delivery--;

Col. 1, Line 25, "such miniature drug delivery pump use" should read
--such miniature drug delivery pump uses--;

Col. 1, Line 29, "due the" should read --due to the--;

Col. 2, Line 39, "a pump drive use to" should read --a pump drive used to--; and Col. 9, Line 25, "further be support" should read --further be supported--.

Signed and Sealed this
Twenty-ninth Day of April, 2014

Michelle K. Lee
*Deputy Director of the United States Patent and Trademark Office*